United States Patent [19]
Reeve et al.

[11] Patent Number: 5,986,132
[45] Date of Patent: Nov. 16, 1999

[54] SYNTHESIS OF CARBOXYLIC ACID DERIVATIVES

[75] Inventors: Maxwell Reeve; Stephen Arthur Bowles, both of Oxford, United Kingdom

[73] Assignee: British Biotech Pharmaceuticals Ltd., Oxford, United Kingdom

[21] Appl. No.: 09/068,676

[22] PCT Filed: Nov. 18, 1996

[86] PCT No.: PCT/GB96/02820

§ 371 Date: May 14, 1998

§ 102(e) Date: May 14, 1998

[87] PCT Pub. No.: WO97/19050

PCT Pub. Date: May 29, 1997

[30] Foreign Application Priority Data

Nov. 18, 1995 [GB] United Kingdom .................... 9523637

[51] Int. Cl.⁶ .................................................. C07C 229/26
[52] U.S. Cl. ............................. 562/564; 546/309; 560/39; 560/41; 562/565; 562/621; 558/414
[58] Field of Search ................................. 546/309; 560/39, 560/41; 562/564, 565, 621; 558/414

[56] References Cited

FOREIGN PATENT DOCUMENTS 9402447  2/1994  WIPO .

OTHER PUBLICATIONS

Griesbeck et al, Helv. Chim. Acta, pp. 1326–1332, vol. 70, 1987.
Rosenmund et al, Archiv Der Pharmazie, vol. 287, No. 8, pp. 441–446, 1954.

*Primary Examiner*—Shailendra Kumar
*Attorney, Agent, or Firm*—Banner & Witcoff, Ltd.

[57] ABSTRACT

Compounds of formula (I) wherein $R_1$, $R_2$, $R_3$, $R_4$, X are as defined in the specification and are prepared by elimination of one of the groups $X_1$ and $X_2$ from a compound of formula (II) wherein $X_1$ and $X_2$ each independently represent a carboxylic acid group or salt thereof, or a protected carboxylic acid group, the non-eliminated group $X_1$ or $X_2$ corresponding to the group X in the desired compound of formula (I).

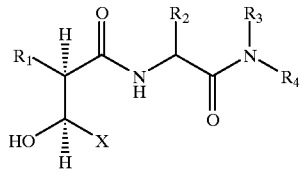

(I)

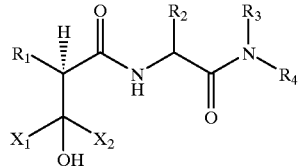

(II)

6 Claims, No Drawings

SYNTHESIS OF CARBOXYLIC ACID DERIVATIVES

This application is a 371 of PCT\GB96\02820, filed Nov. 18, 1996.

The present invention relates to a process for the preparation of biologically active carboxylic acid derivatives, especially matrix metalloproteinase inhibitors, and intermediates for such compounds.

BACKGROUND TO THE INVENTION

Compounds which have the property of inhibiting the action of metalloproteinases involved in connective tissue breakdown such as the collagenases, stromelysins and gelatinases (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. It has been found that hydroxamic acid MMP inhibitors can also inhibit the production of the cytokine tumour necrosis factor ("TNF"). Compounds which inhibit the production or action of TNF are thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Metalloproteinases are characterised by the presence in the structure of a zinc(II) ionic site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1. Many known MMP inhibitors are peptide derivatives, based on naturally occuring amino acids, and are analogues of the cleavage site in the collagen molecule. Other known MMP inhibitors are less peptidic in structure, and may more properly be viewed as pseudopeptides or peptide mimetics. Such compounds usually have a functional group capable of binding to the zinc (II) site in the MMP, and known classes include those in which the zinc binding group is a hydroxamic acid, carboxylic acid, sulphydryl, and oxygenated phosphorus (eg phosphinic acid and phosphonamidate including aminophosphonic acid) groups.

Two known classes of pseudopeptide or peptide mimetic MMP inhibitors have a hydroxamic acid group and a carboxylic group respectively as their zinc binding groups. With a few exceptions, such known MMPs may be represented by the structural formula (A)

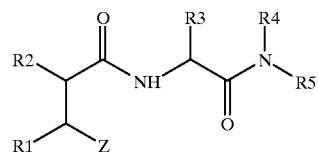

(A)

in which Z is the zinc binding hydroxamic acid (—CONHOH) or carboxylic acid (—COOH) group and the groups $R_1$ to $R_5$ are variable in accordance with the specific prior art disclosures of such compounds. Examples of patent publications disclosing such structures are given below.

The following patent publications disclose hydroxamic acid- and/or carboxylic acid-based MMP inhibitors:

U.S. Pat. No. 4,599,361 (Searle)
EP-A-2321081 (ICI)
EP-A-0236872 (Roche)
EP-A-0274453 (Bellon)
WO 90/05716 (British Biotech)
WO 90/05719 (British Biotech)
WO 91/02716 (British Biotech)
WO 92/09563 (Glycomed)
U.S. Pat. No. 5,183,900 (Glycomed)
U.S. Pat. No. 5,270,326 (Glycomed)
WO 92117460 (SB)
EP-A-0489577 (Celltech)
EP-A-0489579 (Celltech)
EP-A-0497192 (Roche)
U.S. Pat. No. 5256657 (Sterling)
WO 92/13831 (British Biotech)
WO 92/22523 (Research Corp)
WO 93109090 (Yamanouchi)
WO 93/09097 (Sankyo)
WO 93/20047 (British Biotech)
WO 93/24449 (Celltech)
WO 93124475 (Celltech)
EP-A-0574758 (Roche)
EP-A-0575844 (Roche)
WO 94/02446 (British Biotech)
WO 94/02447 (British Biotech)
WO 94/21612 (Otsuka)
WO 94/21625 (British Biotech)
WO 94124140 (British Biotech)
WO 94/25434 (Celltech)
WO 94/25435 (Celltech
WO 95/04033 (Celltech)
WO 95/04735 (Syntex)
WO 95/04715 (Kanebo)
WO 95/09841 (British Biotech)
WO 95/12603 (Syntex)
WO 95/19956 (British Biotech)
WO 95/19957 (British Biotech)
WO 95/19961 (British Biotech)
WO 95/19965 (Glycomed)
WO 95123790 (SB)

BRIEF DESCRIPTION OF THE INVENTION

One interesting subclass of pseudopeptide hydroxamic- and carboxylic acid-based MMP inhibitors has a hydroxy group as the $R_1$ substituent of formula (A). These hydroxy-substituted compounds are accessible via the multistage syntheses described in the literature relating to the compounds in question (see, eg, WO 94/02446, WO 94/02447, WO 95/19956 and WO 95/19961). However, the known methods of synthesis are not optimum, and there is a continuing need for new synthetic routes which provide more efficient and/or stereoselective access to these compounds. The present invention provides such a route, based on the reaction between a lactone and an alpha amino acid derivative to prepare an intermediate which may then be further manipulated chemically to provide desired compounds of, for example, type (A) above wherein $R_1$ is hydroxy, and $R_1$–$R_5$ are a variety of substituents known to be useable in hydroxamic- and carboxylic acid-based MMP inhibitors of the type (A) disclosed in the patent publications listed above.

DETAILED DESCRIPTION OF THE INVENTION

According to the present invention there is provided a process for the preparation of a compound of formula (I)

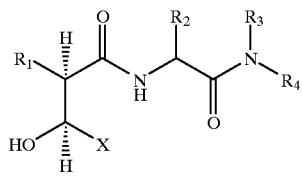

(I)

wherein $R_1$ is a $(C_1$–$C_6)$alkyl, $(C_2$–$C_6)$alkenyl, $(C_2$–$C_6)$alkynyl, phenyl$(C_1$–$C_6)$alkyl, phenyl$(C_1$–$C_6)$alkoxy$(C_1$–$C_6)$alkyl, phenoxy$(C_1$–$C_6)$alkyl, heteroaryl$(C_1$–$C_6)$alkyl, heteroaryl$(C_1$–$C_6)$alkoxy$(C_1$–$C_6)$alkyl, heteroaryloxy$(C_1$–$C_6)$alkyl, cycloalkyl$(C_1$–$C_6)$alkyl or cycloalkenyl$(C_1$–$C_6)$ alkyl group, any one of which may be optionally substituted by one or more substituents selected from $(C_1$–$C_6)$alkyl, —$O(C_1$–$C_6)$alkyl, —$S(C_1$–$C_6)$alkyl, halo and cyano (—CN)

$R_2$ is the characterising group of a natural or non-natural α amino acid in which any functional groups may be protected;

$R_3$ is hydrogen or a $(C_1$–$C_6)$alkyl group;

$R_4$ is hydrogen; $(C_1$–$C_6)$alkyl; $(C_1$–$C_4)$perfluoroalkyl; a group D-$(C_1$–$C_6$ alkyl)- wherein D represents hydroxy, $(C_1$–$C_6)$alkoxy, $(C_1$–$C_6)$alkylthio, acylamino, optionally substituted phenyl or heteroaryl, —$NH_2$, or mono- or di-$(C_1$–$C_6$ alkyl)amino; or a phenyl or heteroaryl ring wherein any ring nitrogen atom may be oxidised as an N-oxide, which may be optionally fused to a benzene ring or to a heterocyclic ring, and wherein any of the rings may be optionally substituted by:

(a) one or more substituents independently selected from hydroxyl, halogen, —CN, —$CO_2H$, —$CO_2(C_1$–$C_6)$alkyl, -$(C_1$–$C_6)$alkyl-$CO_2(C_1$–$C_6)$alkyl, —$CONH_2$, —$CONH(C_1$–$C_6)$alkyl, —$CON((C_1$–$C_6)$alkyl$)_2$, —CHO, —$CH_2OH$, —$(C_1$–$C_4)$perfluoroalkyl, —$O(C_1$–$C_6)$alkyl, —$S(C_1$–$C_6)$alkyl, —$SO(C_1$–$C_6)$alkyl, —$SO_2(C_1$–$C_6)$alkyl, —$NO_2$, —$NH_2$, —NH$(C_1$–$C_6)$alkyl, —$N((C_1$–$C_6)$alkyl$)_2$, or —NHCO$(C_1$–$C_6)$alkyl, or (b) a group selected from $(C_1$–$C_6)$alkyl, $(C_2$–$C_6)$alkenyl, $(C_2$–$C_6)$alkynyl, $(C_3$–$C_8)$cycloalkyl, $(C_4$–$C_8)$cycloalkenyl, phenyl, benzyl, heteroaryl or heteroarylmethyl any of which groups may be optionally substituted with one or more substituents selected from halogen, hydroxyl, amino, carboxyl, $(C_1$–$C_4)$perfluoroalkyl, $(C_1$–$C_6)$alkyl, —$O(C_1$–$C_6)$alkyl or —$S(C_1$–$C_6)$alkyl; and X represents a carboxylic acid group or salt thereof, or a protected carboxylic acid group; which process comprises elimination of one of the groups $X_1$ and $X_2$ from a compound of formula (II)

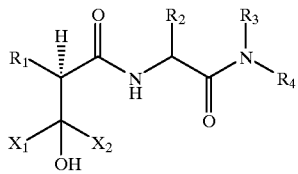

(II)

wherein $R_1$, $R_2$, $R_3$, and $R_4$, are as defined above in relation to formula (I), and $X_1$ and $X_2$ each independently represent a carboxylic acid group or salt thereof, or a protected carboxylic acid group, the non-eliminated group $X_1$ or $X_2$ corresponding to the group X in the desired compound of formula (I).

The elimination of the group $X_1$ or $X_2$ from compound (II) (decarboxylation) may be effected by heating the compound of formula (II), preferably in a compatable liquid medium. The temperature and time of the reaction is not generally critical, provided extreme conditions likely to degrade the reaction components are avoided. In general reaction temperatures of from 20–60° C. and reaction times of from 1–24 hours will be suitable.

The stereochemical configuration of the C atom carrying the $R_1$ group in compound (II) is R, as shown. The decarboxylation of (II) in accordance with the invention results in the end product (I) in which the C atom carrying the OH group has the S configuration as shown, as the predominant stereoisomer.

Compounds of formula (I) wherein X is a carboxylic acid group or a salt thereof are useful as MMP inhibitors in there own right, or as intermediates for conversion to the corresponding hydroxamic acids, eg as described in WO 94/02446 and WO 94/02447.

The compound of formula (II) used in the decarboxylation reaction according to the invention is preferably prepared by the reaction of a lactone of formula (ill) with an amino acid derivative of formula (IV) or an acid addition salt thereof

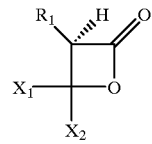

(III)

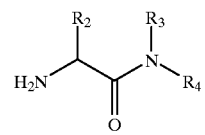

(IV)

wherein $R_1$, $R_2$, $R_3$, and $R_4$, $X_1$ and $X_2$, are as defined in relation to formula (II).

The reaction of compounds (III) and (IV) may be carried out in a compatable solvent, preferably an aprotic solvent. If the amine (IV) is reacted as an acid addition salt, a base may be present in the reaction medium to neutralise the released acid. The temperature and time of the reaction is not generally critical, provided extreme conditions likely to degrade the reaction components or product are avoided. In general reaction temperatures of from 20–60° C. and reaction times of from 1–24 hours will be suitable.

The stereochemical configuration of the C atom carrying the $R_1$ group in the lactone (III) is R, as shown. The C atom carrying the $R_2$ group in the amino acid derivative (IV) is preferably S, since the preferred configuration of that C atom in the ultimate product (I) is also S. The configuration of that C atom is normally unaffected by the reaction of (IV) with (III), but if desired any resultant compound (II) in which that C atom is in the R configuration may be removed by differential solubility, or chromatographic techniques in the usual way.

In compounds (II) or (III), the groups X, $X_1$ and $X_2$ may be protected carboxylic acid groups. Carboxylic acid protecting groups are of course well known, eg from the art of peptide synthesis, and are discussed in the widely used handbook by T. W. Greene and P. G. M. Wuts, Protective groups in Organic Synthesis, 2nd Edition, Wiley, New York 1991, and elsewhere in the chemical literature. Specific examples of carboxylic acid protecting groups include allyl, tert-butyl, and benzyl, optionally substituted in the phenyl ring by one or more nitro or methoxy substituents, for example 4-methoxybenzyl or 2,4-dimethoxybenzyl. Depending on the identity of the carboxylic acid protecting group, it will be removable by acid or base hydrolysis, or by hydrogenation.

In the reaction of lactone (III) with amino acid derivative (IV), if one or each of the groups $X_1$ and $X_2$ is a protected carboxylic acid group, then after reaction of the lactone (II) with the amino acid derivative (IV) one or each of the protected carboxylic acid groups may deprotected, and the resultant compound (II) having one or each of $X_1$ and $X_2$ as carboxylic acid groups may be decarboxylated to prepare a compound (I).

The intermediates of formula (II) and (III) as defined and discussed above are novel structures in there own right, and constitute a further aspect of the present invention.

As used herein the term "($C_1$–$C_6$)alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, pentyl and hexyl.

The term "($C_2$–$C_6$)alkenyl" means a straight or branched chain alkenyl moiety having from 2 to 6 carbon atoms at least one double bond of either E or Z stereochemistry where applicable. This term would include, for example, vinyl, allyl, 1- and 2-butenyl and 2-methyl-2-propenyl.

The term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" means an unsaturated alicyclic moiety having from 3–8 carbon atoms and includes, for example, cyclohexenyl, cyclooctenyl, cycloheptenyl, cyclopentenyl, cyclobutenyl and cyclopropenyl. In the case of cycloalkenyl rings of from 5–8 carbon atoms, the ring may contain more than one double bond.

The unqualified term "heterocyclyl" or "heterocyclic" means (i) a 5–7 membered heterocyclic ring containing one or more heteroatoms selected from S, N and O, and optionally fused to a benzene ring, including for example, pyrrolyl, furyl, thienyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin-4-yl, 3-methyl-2,5-dioxo-1-imidazolidinyl and 3,4,4-trimethyl-2,5-dioxo-1-imidazolidinyl.

The unqualified term "heteroaryl" means a 5–7 membered substituted or unsubstituted aromatic heterocyclic ring.

Unless otherwise specified in the context in which it occurs, the term "substituted" as applied to any moiety herein means substituted with up to four substituents, each of which independently may be ($C_1$–$C_6$)alkyl, ($C_1$–$C_6$) alkoxy, hydroxy, mercapto, ($C_1$–$C_6$)alkylthio, amino, halo (including fluoro, chloro, bromo and iodo), nitro, trifluoromethyl, —COOH, —CONH$_2$, —CN, —COOR$^A$ or —CONHR$^A$R$^A$ wherein R$^A$ is a ($C_1$–$C_6$)alkyl group or the residue of a natural alpha-amino acid.

The term "characterising group of an alpha-amino acid" means the characteristic side chain attached to the —CH (NH$_2$)(COOH) moiety in an alpha-amino acid. Natural alpha-amino acids include the following: glycine, alanine, valine, leucine, isoleucine, phenylaianine, tyrosine, tryptophan, serine, threonine, cysteine, methionine, asparagine, glutamine, lysine, histidine, arginine, glutamic acid and aspartic acid.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R^2$ in the compound of formula (II) or (III) is one of those side chains, the functional substituent may optionally be protected.

The term "protected" when used in relation to a functional substituent in a side chain of an alpha-amino acid means a derivative of such a substituent which is substantially non-functional. In this context, protected amino groups include amido and acylamino, protected hydroxy or mercapto groups include ethers and thioethers, protected carboxyl groups include esters, and imidazolyl, indolyl or guanidyl groups may be protected as t-butoxycarbonyl derivatives. These are only examples of the many protecting derivatives known in the art, and others will be known to the skilled man.

As stated, the process and intermediates of the invention are useful for the preparation of compounds (I) which when X is a carboxylic acid group are MMP inhibitors, and when X is a protected carboxylic acid group can be deprotected to prepare the corresponding carboxylic acid MMP inhibitors. In addition, compounds (I) wherein X is a carboxylic acid group can be converted by known methods to the corresponding hydroxamic acids, which are also MMP inhibitors. It will therefore be appreciated that the identity of the groups $R_1$, $R_2$, $R_3$, and $R_4$ in compounds (II) and (III) will be selected according to the intended structure of the intended MMP inhibitor end product. Those groups may therefore be chosen from amongst those found in the corresponding positions of known MMP inhibitors of analagous structure. Thus:

$R_1$ may for example be n-pentyl, n-hexyl, n-heptyl, n-octyl, n-nonyl, n-decyl, cyclohexylpropyl, phenylpropyl, 4-chlorophenylpropyl, 4-methylphenylpropyl, 4-methoxyphenylpropyl, phenylbutyl, propyloxymethyl and propylsulphanyl, or in particular isobutyl;

$R_2$ may for example be a group $R_7$—(B)$_n$— wherein n is 0 or 1, B represents a divalent straight or branched, saturated or unsaturated hydrocarbon chain of up to 6 C atoms which may be interrupted by an O or S atom, and $R_7$ is —CONHOH, carboxyl, esterified or amidated carboxyl, cycloalkyl, cycloalkenyl, heterocyclyl, phenyl, napthyl, or substituted phenyl or napthyl in which the substituent(s) are selected from phenyl, hydroxy, $C_1$–$C_6$ alkoxy, benzyloxy, or $R_8$—(C=O)—($C_1$–$C_6$alkyl)—O— wherein $R_8$ is hydroxy, amino, or an amino acid residue linked via an amide bond; or (except when n=0) $R_7$ is hydrogen;

—CH($C_1$–$C_4$ perfluoroalkyl)$_2$;
—C($C_1$–$C_4$ perfluoroalkyl)$_3$; or
—C($C_1$–$C_6$ alkyl)$_2$$R^{11}$ or a 3 to 8 membered cycloalkyl group substituted by ($C_1$–$C_6$)alkyl or $R^{11}$ at the alpha-position, wherein
$R^{11}$ is —OH, —SH, halogen, ($C_1$–$C_4$)perfluoroalkyl, —CH$_2$OH, —CO$_2$H, —CO$_2$($C_1$–$C_6$)alkyl, optionally substituted phenyl or optionally substituted heteroaryl, —O($C_1$–$C_6$ alkyl), —S($C_1$–$C_6$ alkyl), —SO($C_1$–$C_6$ alkyl), —SO$_2$($C_1$–$C_6$ alkyl), —OPh, —OCH$_2$Ph, —SPh, —SOPh, —SO$_2$Ph, —SCH$_2$Ph, —SOCH$_2$Ph, or —SO$_2$CH$_2$Ph, cyclohexylmethylsulphanyl, cyclohexylmethylsulphinyl, or cyclohexylmethylsulphonyl in which any of the foregoing Ph (phenyl) or cyclohexyl groups may be substituted, for example by —OH or —O($C_1$–$C_6$ alkyl) or halogen; and examples of particular $R^2$ groups include, 4-methoxyphenylmethyl, cyclohexylmethyl, 2-thienylmethyl, (4-hydroxycarbonylmethoxy)-phenylmethyl, (4-phenyl)phenylmethyl, methoxycarbonylethyl, N-hydroxyaminocarbonylethyl 1,1-diethylprop-1-yl, 1-cyclopropyl-ethyl, adamant-1-yl, 1,1,1,3,3,3-hexafluoroprop-2-yl, 2-hydroxyprop-2-yl, 2-mercaptoprop-2-yl, 2-methoxyprop-2-yl, 2-carboxyprop-2-yl, 2-methoxycarbonylprop-2-yl, 2-(2-methoxyethoxymethoxy)prop-2-yl, 2-(tetrahydropyran-4-yl)prop-2-yl, 2-(tetrahydrofuran-2-yl)prop-2-yl, 1-hydroxy-cyclopent-1-yl, 2-(4-methoxy-benzylsulphinyl)prop-2-yl, 2-(4-methoxybenzylsulphonyl) prop-2-yl, 2-cyclohexylmethylsulphanyl-prop-2-yl, cyclohexylmethylsulphinyl-prop-2-yl, cyclohexylmethylsulphanyl-prop-2-yl, diphenylmethyl or 2-phenylprop-2-yl; and particularly tert-butyl, benzyl, 2-fluoroprop-2-yl, 2-methylsulphanylprop-2-yl, 2-methylsulphinyl-prop-2-yl, 2-methylsulphonylprop-2-yl, 2-mercaptoprop-2-yl, 2-benzylsulphanyl-prop-2-yl, 2-benzylsulphinylprop-2-yl, cyclohexylmethylsulphanylprop-2-yl and 2-(4-methoxybenzylsulphinyl)prop-2-yl;

$R_3$ may for example be hydrogen or methyl;

$R_4$ may for example be hydrogen, ethyl, propyl, n-butyl, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetyl-aminoethyl, 3-(2-pyrrolidone)propyl, optionally substituted phenylethyl, phenylpropyl, phenylbutyl, phenylpentyl; or optionally substituted phenyl, napthyl, furanyl, thienyl, pyrrolinyl, tetrahydrofuranyl, imidazolyl, oxadiazolyl, thiazolyl, thiadiazolyl, pyridinyl, pyridinyl N-oxides, piperazinyl, indolyl, benzimidazolyl, benzotriazolyl, pyrazinyl, pyridazinyl, pyrimidinyl, dithianyl, benzo[b]thienyl, isoxazolyl or quinolinyl; and particularly methyl, t-butyl, benzyl, phenyl, 3-methoxyphenyl, pyridin-2-yl, pyridin-3-yl, and thiazol-2-yl, 4,5-dimethylthiazol-2-yl, 5-bromothiazol-2-yl, 4-ethoxycarbonylmethyl-thiazol-2-yl, 5-methyl-1,3,4-thiadiazol-2-yl or 4-tertbutylthiazol-2-yl;

In particular, the process of the invention is suitable for the preparation of compounds (I) wherein $R_1$ is isobutyl, $R_2$ is tert-butyl or 2-mercapto-2-methylpropyl, $R_3$ is hydrogen, and $R_4$ is methyl or 2-pyridinyl, particularly such compounds wherein the C atom carrying the $R_2$ group is in the S configuration.

The lactone (III) starting materials may be prepared by treating succinic acid derivatives of formula (V) with bromine, to form the lactone ring with elimination of HBr:

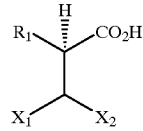

(V)

the substituents $R_1$, X, and $X_2$ being as defined for formula (III).

The amino acid derivative (IV) starting materials are either known compounds or are accessible by standard synthetic methods.

The following examples illustrate the use of the process of the invention.

EXAMPLE 1

Preparation of MMP Inhibitors 3R-(2,2-Dimethyl-1S-methylcarbamoyl-propylcarbamoyl)-2S-hydroxy-5-methyl-hexanoic acid (7) and 3R-(2,2-Dimethyl-1S-methylcarbamoyl-propylcarbamoyl)-2S-hydroxy-5-methyl-hexano-hydroxamic acid (9)

Step 1

3R-Isobutyl-4-oxo-oxetane-2,2-dicarboxylic acid dibenzyl ester (1) and 2-benzyloxycarbonyl-2-bromo-3S-isobutyl-succinic acid-1-benzyl ester (2)

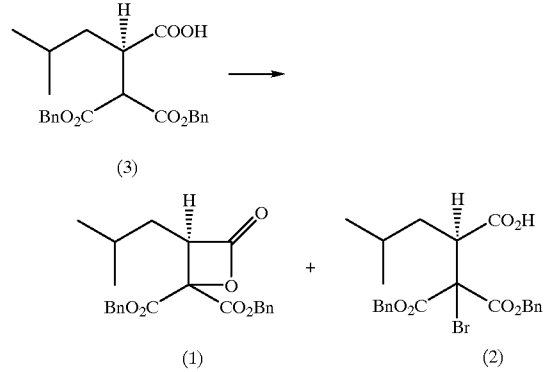

Sodium hydride (2.0 g, 50 mmol, 60% disp) was added to a solution of 2-benzyloxycarbonyl-3R-isobutyl-succinic acid 1-benzyl ester (3)(10.0 g, 25 mmol) in tetrahydrofuran (100 mL) at 0° C. After 1 hour bromine (1.28 mL, 25 mmol) was added dropwise. The orange reaction mixture was stirred at room temperature overnight. The reaction mixture was partitioned between ethyl acetate and water. The organic layer was washed with brine, dried (MgSO$_4$) and evaporated to give an orange oil. This was absorbed onto silica and purified by column chromatography on silica eluting with a gradient of 0–100% ethyl acetate in hexane. Evaporation of the appropriate fractions gave the lactone (1) as a colourless oil which solidified on standing (7.67 g, 19.3 mmol, 77%); $v_{max}$ (solution) 2965, 1848, 1749, 1499 and 1458cm$^{-1}$; $\delta_H$(CDCl$_3$) 0.80 (3H, d, J=6.5 Hz), 0.83 (3H, d, J=6.5 Hz), 1.44 (2H, m), 1.67 (1H, m ), 4.34 (1H, t, J=8.25 Hz), 5.26 (4H, m) and 7.35 (10H, m); $\delta_C$(CDCl$_3$) 167.7, 165.0, 164.6, 134.3, 134.1, 128.8, 128.6, 128.6, 128.2, 68.5, 68.4, 57.5, 33.6, 25.5, 21.9, and 21.9; C$_{23}$H$_{24}$O$_6$ requires C:69.68, H:6.10, found C:69.69, H:6.08; $[\alpha]_D^{20.0°}$ $^{C:}$=+41.1°,(c=2, MeOH) and the bromide (2) as a yellow oil (1.35 g, 2.8 mmol, 11%); $v_{max}$ 2958, 1744, 1456 and 1232 cm$^{-1}$; $\delta_H$(CDCl$_3$) 0.77 (3H, d, J=6.4 Hz), 0.83 (3H, d, J=6.6 Hz), 1.61–1.83 (3H, m), 3.48 (1H, m), 5.17 (4H, m) and 7.32 (10H, m); $\delta_C$ (CDCl$_3$) 177.1, 165.7, 165.3, 134.4, 134.3, 128.5, 128.2, 128.1, 68.9, 68.7, 63.0, 50.5, 39.0, 26.3, 23.4 and 20.9.

Step 2

2-[1R-(2,2-Dimethyl-1S-methylcarbamoyl-propylcarbamoyl)-3-methyl-butyl]-2-hydroxy-malonic acid dibenzylester (5)

Method 1

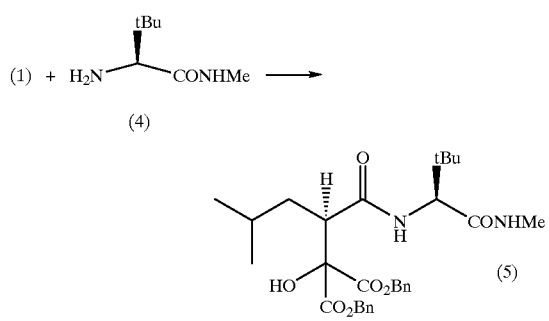

3R-Isobutyl-4-oxo-oxetane-2,2-dicarboxylic acid dibenzyl ester (1)(1.0 g, 2.52 mmol) in tetrahydrofuran (10 mL) was treated with 2S-amino-3,3,N-trimethyl-butyramide (4) (399 mg, 2.77 mmol) and the solution was aged at room temperature for 7 days. The solution was partitioned between ethyl acetate and hydrochloric acid (1 M). The organic layer was washed with brine, dried (MgSO$_4$) and evaporated to give a white foam (1.32 g, 2.4 mmol, 97%); 6H(CDCl$_3$) 0.77 (3H, d, J=6 Hz), 0.79 (3H, d, J=6 Hz), 0.98 (9H, s), 1.81–1.27(3H, m), 2.76 (3H, d, J=5.7 Hz), 3.50 (1H, m), 4.10 (2H, m), 5.00–5.28 (4H, m), 5.72 (1H, m), 6.80 (1H, d, J=9.3 Hz) and 7.29–7.32 (10H, m).

Method 2

3R-Isobutyl4-oxo-oxetane-2,2-dicarboxylic acid dibenzyl ester (1)(2.48 g, 6.26 mmol) in tetrahydrofuran (10 mL) was treated with 2S-amino-3,3,N-trimethyl-butyramide (4)(992 mg, 6.89 mmol) and the solution was aged at room temperature overnight. The solution was partitioned between ethyl acetate and hydrochloric acid (2M). The organic layer was washed with brine, dried (MgSO$_4$) and evaporated to give a white foam (3.13 g, 92%); Structure was confirmed by NMR.

Step 3

2-[1R-(2,2-Dimethyl-1S-methylcarbamoyl-propylcarbamoyl)-3-methyl-butyl]-2-hydroxy-malonic acid (6)

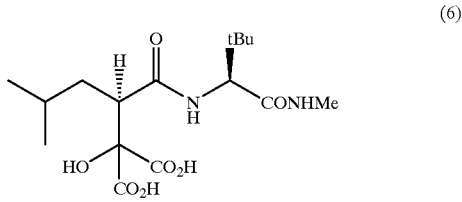

2-[1R-(2,2-Dimethyl-1S-methylcarbamoyl-propylcarbamoyl)-3-methyl-butyl]-2-hydroxy-malonic acid dibenzyiester (5)(161 mg, 0.3 mmol) was dissolved in ethanol (5 mL). 5% Palladium on carbon (16 mg, 10% by wt) was added and the mixture was hydrogenated at atmospheric pressure and room temperature for 2 hours. The catalyst was filtered onto Kieselguhr and the solvent removed under reduced pressure to give the product as a white solid (76 mg, 0.21 mmol, 70%); $\delta_H$ (d$_6$-DMSO) 0.65–0.73 (6H, m), 0.75 (9H, s), 1.0–1.5 (3H, m), 2.41 (3H, d, J=6.0 Hz), 2.95 (1H, m), 3.95 (1H, d) and 7.63–7.80 (2H, m).

Step 4

3R-(2,2-Dimethyl-1S-methylcarbamoyl-propylcarbamoyl)-2S-hydroxy-5-methyl-hexanoic acid (7)

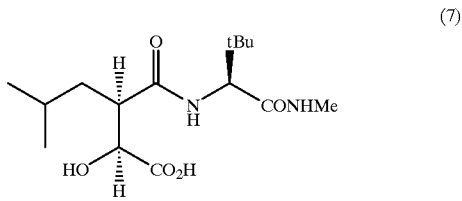

Route 1

2-[1R-(2,2-Dimethyl-1S-methylcarbamoyl-propylcarbamoyl)-3-methyl-butyl]-2-hydroxy-malonic acid (6)(76 mg, 0.21 mmol) was heated at reflux in toluene (2 mL) for 2 hours. The toluene was then removed under reduced pressure to give the product as a white foam (58 mg, 0.18 mmol, 87%); 6H(d$_6$-DMSO) 0.82 (6H, m), 0.88 (9H, s), 1.4 (1H, m), 1.47 (2H, m), 2.54 (3H, d, J=4.4 Hz), 2.69 (1H, m), 3.90 (1H, d, J=6.8 Hz) and 4.00 (1H, d, J=9.5 Hz).

Route 2

2-[1R-(2,2-Dimethyl-1S-methylcarbamoyl-propylcarbamoyl)-3-methyl-butyl]-2-hydroxy-malonic acid dibenzylester (5)(820 mg, 1.5 mmol) in toluene (10 mL) was treated with 5% palladium on carbon (82 mg, 10% by wt) and hydrogenated at 60 psi and 75° C. overnight. The reaction mixture was cooled. The catalyst was filtered onto Kieselguhr and the solvent removed under reduced pressure to give the product as a colourless glass (443 mg, 1.4 mmol, 93%). $^1$H NMR as above.

Step 5

N 1-Benzyloxy-N 4-(2,2-dimethyl-1S-methylcarbamoyl-propyl)-2S-hydroxy-3R-isobutyl-succinamide (8)

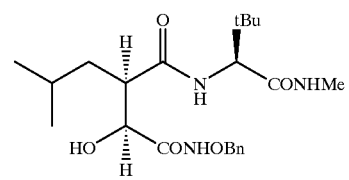
(8)

3R-(2,2-Dimethyl-1S-methylcarbamoyl-propylcarbamoyl)-2S-hydroxy-5-methyl-hexanoic acid (7) (443 mg, 1.4 mmol) in tetrahydrofuran (4 mL) and water (2 mL) was treated with O-benzylhydroxylamine hydrochloride (358 mg, 2.24 mmol) and 1-(3-dimethylaminopropyl)-3-ethylcarbodiimide hydrochloride (579 mg, 2.94 mmol). Stirring was continued at room temperature overnight. The solvent was removed under reduced pressure. The product was extracted into ethyl acetate, washed with hydrochloric acid (1M), sodium bicarbonate and brine, dried (MgSO$_4$) and evaporated under reduced pressure to give a pale yellow foam (573 mg, 1.36 mmol, 97%); $\delta_H$ (d$_6$-DMSO) 0.79 (6H, m), 0.89 (9H, s), 1.0–1.3 (3H, m), 2.55 (3H, d, J=4.6 Hz), 2.71 (1H, m) 3.75 (1H, t, J=7.6 Hz), 4.17 (1H, d, J=9.6 Hz), 4.78 (2H, s), 5.41 (1H, d, J=7.5 Hz), 7.24 (5H, m), 7.34 (1H, d, J=9.4 Hz) and 7.72 (1H, m).

Step 6
3R-(2,2-Dimethyl-1S-methylcarbamoyl-propylcarbamoyl)-2S-hydroxy-5-methyl-hexano-hydroxamic acid (9)

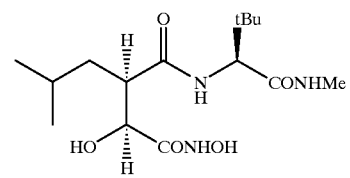
(9)

N 1-Benzyloxy-N 4-(2,2-dimethyl-1S-methylcarbamoyl-propyl)-2S-hydroxy-3R-isobutyl-succinamide (8) (573 mg, 1.36 mmol) in ethanol (10 mL) was treated with 10% palladium on carbon (57 mg, 10% by wt) and hydrogenated at room temperature and atmospheric pressure over 2 days. The catalyst was filtered onto Kieselguhr and the solvent evaporated to give a pale brown solid (419 mg, 1.26 mmol, 93%); $\delta_H$(d6-DMSO) 0.63 (3H, m), 0.72 (9H, s), 1.25 (3H, m), 2.40 (3H, d, J=4.5 Hz), 2.51 (1H, m), 3.70 (1H, t), 3.97 (1H, d, J=9.4 Hz), 5.37 (1H, d), 7.37 (1H, d, J=9.4 Hz) and 7.74 (1H, m).

EXAMPLE 2

2S-Amino-N-methyl-3-(4-naphthalene-1-yl-phenyl)-propionamide hydrochloride (13)

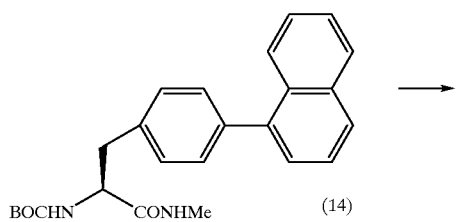
(14)

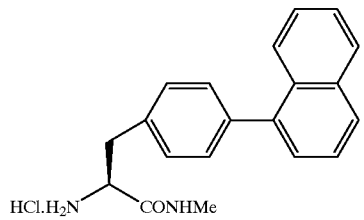
(13)

[1S-Methylcarbamoyl-2-(4-naphthalen-1-yl-phenyl)-ethyl]carbamic acid tert-butyl ester (14)(500 mg, 1.28 mmol) was dissolved in ethanol (5 mL). Hydrogen chloride gas was bubbled through the solution for 10 minutes. The solvent was evaporated under reduced pressure to give a yellow foam (473 mg, 1.39 mmol, >100%); $\delta_H$(CDCl$_3$) 2.70 (3H, bs), 3.4–3.6 (3H, m), 4.80 (1H, bs) and 7.1–8.6 (11H, m).

2-Hydroxy-2-{3-methyl-1R-[1S-methylcarbamoyl-2-(4-naphthalen-1-yl)-phenyl)-ethylcarbamoyl]-butyl}-malonic acid dibenzyl ester (12)

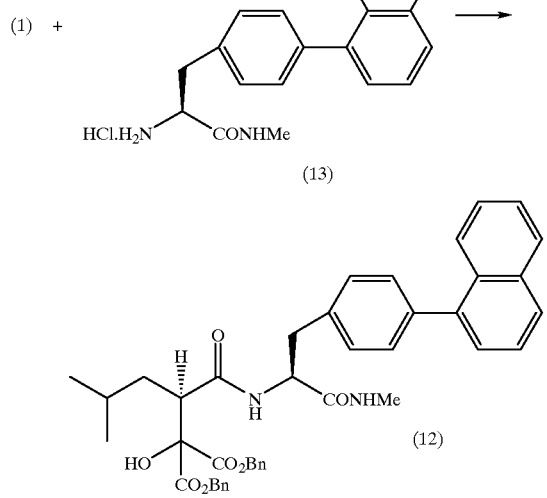

3R-Isobutyl4-oxo-oxetane-2,2-dicarboxylic acid dibenzyl ester (1)(200 mg, 0.5 mmol) in tetrahydrofuran (5 mL) was treated with 2S-amino-N-methyl-3-(4-naphthalen-1-yl-phenyl)-propionamide hydrochloride (13)(187 mg, 0.55 mmol) and 4-methyl morpholine (60 μL, 0.55 mmol). Stirring was continued at room temperature overnight. A precipitate formed. Ethyl acetate and hydrochloric acid (2M) were added. The organic layer was separated, washed with brine, dried (MgSO$_4$) and evaporated to give a pale green oil. This was purified by column chromatography on silica eluting with a gradient of 0–100% ethyl acetate in hexane. Evaporation of the appropiate fractions gave the product as a colourless oil (265 mg, 0.38 mmol, 76%) which by $^1$H NMR contains approximately 13% of a diastereomer; $\delta_H$(CDCl$_3$) 0.66 (3H, d, J=6.6 Hz), 0.72 (3H, d, J=6.4 Hz), 0.86 (2H, m), 1.53 (1H, m,), 2.74 (3H, d, J=4.8 Hz), 3.00–3.45 (3H, m), 4.73 (1H, m), 5.09–5.29 (4H, m), 6.30 (1H, m), 6.73 (1H, d, J=8.0 Hz), 7.22–7.54 (18H, m) and 7.84–7.92 (3H, m).

By the methods of Example 1, steps 3 and 4, (12) is converted to the MMP inhibitor 3R-[1S-methylcarbamoyl- 2-(4-naphthalen-1-yl)-phenyl)-ethylcarbamoyl]-2S-hydroxy-5-methyl-hexanoic acid, which in turn is converted by the methods of Example 1 steps 5 and 6 to the MMP Inhibitor 3R-[1S-methylcarbamoyl-2-(4-naphthalen-1-yl)-phenyl)-ethyicarbamoyl]-2S-hydroxy-5-methyl-hexano-hydroxamic acid.

EXAMPLE 3

2-{1R-[2,2-Dimethyl-1S-(pyridin-2-ylcarbamoyl)-propylcarbamoyl]-3-methyl-butyl}-2-hydroxy-malonic acid dibenzyl ester (10)

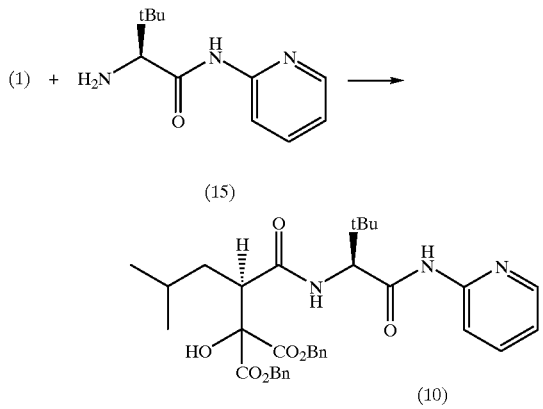

3R-Isobutyl4-oxo-oxetane-2,2-dicarboxylic acid dibenzyl ester (1)(200 mg, 0.5 mmol) in tetrahydrofuran (5mL) was treated with 2S-amino-3,3-dimethyl-N-pyridin-2-yl-butyramide (15)(114 mg, 0.55 mmol). The solution was aged at room temperature overnight. The reaction mixture was partitioned between ethyl acetate and hydrochloric acid (1M). The organic layer was separated, washed with brine, dried (MgSO$_4$) and evaporated to give a yellow oil. This was purified by column chromatography on silica eluting with a gradient of 0–100% ethyl acetate in hexane. Evaporation of the appropriate fractions gave the product as a white solid (255 mg, 0.44 mmol, 89%); $\delta_H$(CDCl$_3$) 0.74 (6H, d, J=6.4 Hz), 1.03 (9H, s), 1.43–1.95 (3H, m), 3.36 (1H, dd, J=3.3, 11.4 Hz), 4.63 (1H, d), 5.20–5.30 (4H, m) 7.17 (1H, bt), 7.20–7.40 (10H, m), 7.75 (1H, bt) and 8.32 (2H, bt).

By the methods of Example 1, steps 3 and 4, (10) is converted to the MMP inhibitor 3R-(2,2-Dimethyl-1S-pyridin-2-ylcarbamoyl-propylcarbamoyl)-2S-hydroxy-5-methyl-hexanoic acid), which in turn is converted by the methods of Example 1 steps 5 and 6 to the MMP Inhibitor 3R-(2,2-Dimethyl-1S-pyridin-2-ylcarbamoyl-propylcarbamoyl)-2S-hydroxy-5-methyl-hexano-hydroxamic acid.

EXAMPLE 4

2-Hydroxy-2-[3-methyl-1R-(1S-methylcarbamoyl-2-phenyl-ethylcarbamoyl)-butyl]-malonic acid dibenzyl ester (11)

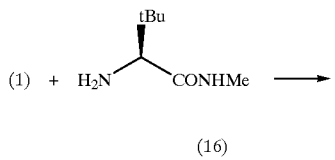

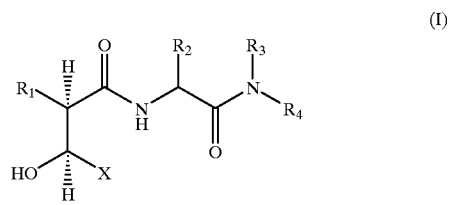

3R-Isobutyl4-oxo-oxetane-2,2-dicarboxylic acid dibenzyl ester (1)(200 mg, 0.5 mmol) in tetrahydrofuran (5 mL) was treated with 2S-amino-N-methyl-3-phenylpropionamide (16) (90 mg, 0.55 mmol) and the reaction was aged at room temperature for 18 hours. The reaction was partitioned between ethyl acetate and hydrochloric acid (1M). The organic layer was separated, washed with brine, dried (MgSO$_4$) and evaporated to dryness under reduced pressure. The crude product was purified by column chromatography on silica eluting with a gradient of 0–100% ethyl acetate in hexane. Evaporation of the appropriate fractions gave the product as a colourless oil (150 mg, 0.26 mmol, 52%); $\delta_H$(CDCl$_3$) 0.66 (6H, m), 0.80–1.45 (3H, m), 2.68 (3H, d, J=4.8 Hz), 2.95–3.22 (3H, m), 4.58 (1H, m), 5.03–5.27 (4H, m), 6.12 (1H, m), 6.60 (1H, d, J=8.6 Hz) and 7.16–7.38 (15H, m).

By the methods of Example 1, steps 3 and 4, (11) is converted to the MMP inhibitor 3R-[1S-methylcarbamoyl-2-phenyl)-ethylcarbamoyl]-2S-hydroxy-5-methyl-hexanoic acid, which in turn is converted by the methods of Example 1 steps 5 and 6 to the MMP Inhibitor 3R-[1S-methylcarbamoyl-2-phenyl)-ethylcarbamoyl]-2S-hydroxy-5-methyl-hexano-hydroxamic acid.

We claim:

1. A process for the preparation of a compound of formula (I)

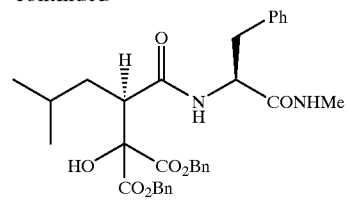

wherein

R$_1$ is a (C$_1$–C$_6$)alkyl, (C$_2$–C$_6$)alkenyl, (C$_2$–C$_6$)alkynyl, phenyl(C$_1$–C$_6$)alkyl, phenyl(C$_1$–C$_6$)alkoxy(C$_1$–C$_6$) alkyl, phenoxy(C$_1$–C$_6$)alkyl, heteroaryl(C$_1$–C$_6$)alkyl, heteroaryl(C$_1$–C$_6$)alkoxy(C$_1$–C$_6$)alkyl, heteroaryloxy (C$_1$–C$_6$)alkyl, cycloalkyl(C$_1$–C$_6$)alkyl or cycloalkenyl (C$_1$–C$_6$) alkyl group, any one of which may be optionally substituted by one or more substituents selected from (C$_1$–C$_6$)alkyl, —O(C$_1$–C$_6$)alkyl, —S(C$_1$–C$_6$) alkyl, halo and cyano (—CN);

R$_2$ is the characterising group of a natural or non-natural a amino acid in which any functional groups may be protected;

R$_3$ is hydrogen or a (C$_1$–C$_6$)alkyl group;

R$_4$ is hydrogen; (C$_1$–C$_6$)alkyl; (C$_1$–C$_6$)perfluoroalkyl; a group D-(C$_1$–C$_6$ alkyl)- wherein D represents hydroxy, (C$_1$–C$_6$)alkoxy, (C$_1$–C$_6$)alkylthio, acylamino, optionally substituted phenyl or heteroaryl, —NH$_2$, or mono- or di-(C$_1$–C$_6$ alkyl)amino; or a phenyl or heteroaryl ring wherein any ring nitrogen atom may be oxidised as an N-oxide, which may be optionally fused to a benzene ring or to a heterocyclic ring, and wherein any of the rings may be optionally substituted by:
(a) one or more substituents independently selected from hydroxyl, halogen, —CN, —CO$_2$H, —CO$_2$(C$_1$–C$_6$)alkyl, -(C$_1$–C$_6$)alkyl-CO$_2$(C$_1$–C$_6$)alkyl, CONH$_2$, —CONH(C$_1$–C$_6$)alkyl, —CON((C$_1$–C$_6$)alkyl)$_2$, —CHO, —CH$_2$OH, —(C$_1$–C$_4$)perfluoroalkyl, —O(C$_1$–C$_6$)alkyl, —S(C$_1$–C$_6$)alkyl, —SO(C$_1$–C$_6$)alkyl, —SO$_2$(C$_1$–C$_6$)alkyl, —NO$_2$, —NH$_2$, —NH(C$_1$–C$_6$)alkyl, —N((C$_1$–C$_6$)alkyl)$_2$, or —NHCO(C$_1$–C$_6$)alkyl, or
(b) a group selected from (C$_1$–C$_6$)alkyl, (C$_2$–C$_6$)alkenyl, (C$_2$–C$_6$)alkynyl, (C$_3$–C$_8$)cycloalkyl, (C$_4$–C$_8$)cycloalkenyl, phenyl, benzyl, heteroaryl or heteroarylmethyl any of which groups may be optionally substituted with one or more substituents selected from halogen, hydroxyl, amino, carboxyl, (C$_1$–C$_4$)perfluoroalkyl, (C$_1$–C$_6$)alkyl, —O(C$_1$–C$_6$)alkyl or —S(C$_1$–C$_6$)alkyl; and X represents a carboxylic acid group or salt thereof, or a protected carboxylic acid group; which process comprises elimination of one of the groups X$_1$ and X$_2$ from a compound of formula (II)

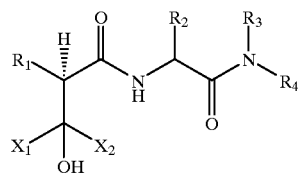

(II)

wherein R$_1$, R$_2$, R$_3$, and R$_4$, are as defined above in relation to formula (I), and X$_1$ and X$_2$ each independently represent a carboxylic acid group or salt thereof, or a protected carboxylic acid group, the non-eliminated group X$_1$ or X$_2$ corresponding to the group X in the desired compound of formula (I).

2. A process as claimed in any claim 1 wherein in compounds (I) and (II) R$_1$ is isobutyl, R$_2$ is tert-butyl or 2-mercapto-2-methylpropyl, R$_3$ is hydrogen, and R$_4$ is methyl or 2-pyridinyl.

3. A process as claimed in claim 1 or claim 2 wherein in compounds (I) and (II) the stereochemical configuration of the carbon atom carrying the R$_2$ group is S.

4. A process as claimed in any one of claims 1 to 3 wherein the elimination of the group X$_1$ or X$_2$ is effected by heating the compound of formula (II).

5. A process as claimed in any one of the preceding claims which includes as a first step the preparation of the compound of formula (II) by a process comprising the reaction of a lactone of formula (III) with an amino acid derivative of formula (IV) or an acid addition salt thereof

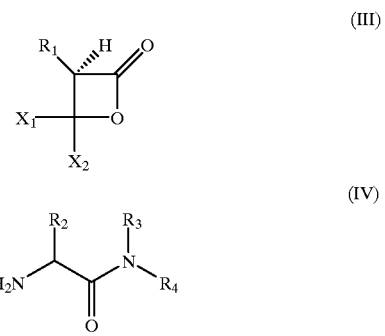

wherein R$_1$, R$_2$, R$_3$, and R$_4$, X$_1$ and X$_2$, and the stereochemical configuration of the carbon atom carrying the R$_2$ group, are as permitted in relation to the compound of formula (II).

6. A process as claimed in claim 5 wherein one or each of the groups X$_1$ and X$_2$ in the lactone of formula (III) is a protected carboxylic acid group, and after reaction of the lactone (II) with the amino acid derivative (IV) one or each of the protected carboxylic acid groups is deprotected.

* * * * *